(12) United States Patent
Matsutani et al.

(10) Patent No.: US 8,826,958 B2
(45) Date of Patent: Sep. 9, 2014

(54) CRIMPING DEVICE FOR ATTACHING A MEDICAL SUTURE THREAD TO A MEDICAL SUTURE NEEDLE

(75) Inventors: Kanji Matsutani, Utsunomiya (JP); Masahiko Saito, Utsunomiya (JP)

(73) Assignee: MANI, Inc., Utsunomiya-shi, Tochigi (JP)

( * ) Notice: Subject to any disclaimer, the term of this patent is extended or adjusted under 35 U.S.C. 154(b) by 423 days.

(21) Appl. No.: 12/527,658

(22) PCT Filed: Feb. 25, 2008

(86) PCT No.: PCT/JP2008/053205
§ 371 (c)(1),
(2), (4) Date: Aug. 18, 2009

(87) PCT Pub. No.: WO2008/105374
PCT Pub. Date: Sep. 4, 2008

(65) Prior Publication Data
US 2010/0032101 A1 Feb. 11, 2010

(30) Foreign Application Priority Data
Feb. 27, 2007 (JP) .................................. 2007-046405

(51) Int. Cl.
*B29C 65/78* (2006.01)
*A61B 17/06* (2006.01)
*A61B 17/00* (2006.01)

(52) U.S. Cl.
CPC . *A61B 17/06004* (2013.01); *A61B 2017/00526* (2013.01)
USPC ......................................... 156/423; 606/224

(58) Field of Classification Search
CPC ...................................................... B29C 65/78
USPC ......................................... 156/423; 606/224
See application file for complete search history.

(56) References Cited

U.S. PATENT DOCUMENTS 5,417,710 A * 5/1995 Matsutani et al. ............ 606/224

FOREIGN PATENT DOCUMENTS

| JP | 055-75309 | 5/1980 |
| JP | 63-212028 A | 9/1988 |
| JP | 3103192 B2 | 10/1991 |
| JP | 5-237125 A | 9/1993 |

* cited by examiner

Primary Examiner — Daniel Lee
(74) Attorney, Agent, or Firm — Smith Patent Office

(57) ABSTRACT

A crimping die including a fixed die and a moving die which moves away from or toward the fixed die, and a thread guide arranged closely to the edge of the stop hole formed in the proximal end face of an eyeless needle held by the crimping die and having a surface for guiding the suture thread to the stop hole. The thread guide is arranged such that an external force does not act on the suture thread on the outside of the stop hole formed in the eyeless needle as a crimping operation progresses when the proximal end face of the eyeless needle is crimped by the crimping die, or arranged to move in the direction in which an external force does not act.

17 Claims, 5 Drawing Sheets

CRIMPING DEVICE FOR ATTACHING A MEDICAL SUTURE THREAD TO A MEDICAL SUTURE NEEDLE

TECHNICAL FIELD

The present invention relates to a crimping device used to bond a suture thread to a stop hole formed in a face of the proximal end of a medical suture needle and, in particular, relates to a crimping device that prevents a shearing force from acting on a suture thread when the area corresponding to a stop hole in the proximal end of a medical suture needle is crimped.

BACKGROUND ART

As a medical suture needle, an eyeless needle is known to have a sharp point at one end and a stop hole formed in a face of the other end (i.e., the proximal end face). In this medical suture needle, one end of a suture thread is inserted into the stop hole formed in the face of the proximal end, and the area of the stop hole corresponding to the depth of the stop hole (i.e., the proximal end) is crimped, thereby bonding the suture thread. Medical suture needles of several types that differ in specification have been provided. However, many of the suture thread needles corresponding to these specifications are set to from approximately 0.14 mm to approximately 1.40 mm in thickness. Generally, the diameter of a stop hole formed in the face of the proximal end of each of such medical suture needles is approximately half the thickness of the needle.

A device for crimping the proximal end of a medical suture needle includes a pair of crimping dies that are driven by a driving device, such as a motor as a representative example, so as to move away from or toward each other. While the leading end of a suture thread is inserted in the stop hole of the suture needle, the proximal end of this needle is supplied between the separated crimping dies. In this state, the crimping dies are moved closer to each other, thereby crimping the area corresponding to the stop hole in the proximal end.

Inserting the leading end of a suture thread into a stop hole formed in the face of the proximal end of a medical suture need is a precise task. Therefore, such a crimping device (e.g., see Patent Document 1) as described below has been proposed. This crimping device is provided with a thread guide so as to correspond to a pair of crimping dies composing the crimping device. While a medical suture needle is held by the crimping dies, a suture thread is guided by the thread guide that has approached the stop hole of the medical suture device, thereby inserting the suture thread into the stop hole.

The crimping device disclosed in the Patent Document 1 includes a lower die fixed to a frame, and an upper die that moves away from or toward the lower die. This device is configured such that the thread guide including a first guide member and a second guide member that have a first face and a second face respectively is disposed opposite a stop hole in an eyeless needle held by the lower and upper dies. In particular, an adjustment is made so that while the side face of each of the guide members is kept in contact with the side face of the lower die, the first and second flat faces serving as guide faces correspond to the position of the edge of a stop hole formed in the face of the proximal end of a medical suture needle held between the upper and lower dies.

Accordingly, a medical suture needle to which a suture thread is to be bonded is supplied between the lower and upper dies, and the face of the proximal end of this needle is brought into contact with the side faces of the guide members. This stabilizes the crimping position of the lower and upper dies from the face of the proximal end. The suture thread slides along the first or second flat face of the thread guide toward the medical suture thread needle held by the lower and upper dies, thereby enabling the suture thread to be guided securely into a stop hole.

Patent Document 1: Japanese Patent No. 3103192

DISCLOSURE OF THE INVENTION

Problems to be Solved by the Invention

In the technology disclosed in the Patent Document 1, while a medical suture needle 51 of uniform thickness is crimped, only the upper die 53 changes its position relative to the lower die 52 and the thread guide 54 without changing the positional relation between the lower die 52 and the thread guide 54, as shown in FIGS. 5A and 5B. Therefore, when the suture needle is crimped by moving the upper die 53 closer to the lower die 52, the size of stop hole 51a decreases by an amount corresponding to the crimping allowance. As its size decreases, the axis of the stop hole 51a displaces toward the lower die 52. Consequently, one end of a suture thread 55 is supported by a guide face 54a composed of the first and second flat faces of the thread guide 54 while the other end is inserted into the stop hole 51a whose size has been reduced. This may lead to the problem of the suture thread's being bent (see, FIG. 5B), and damaged by the thread guide 54. The technology described in the Patent Document 1 overcomes this problem by forming an inclining face on the thread guide 54, which face is opposite the lower die 52.

In the crimping device described above, it is difficult to adjust the positional relation between the thread guide and the edge of a stop hole in a medical suture needle held by the lower and upper dies. That is, adjusting the leading end of the inclining face so as to be located at the same level as the edge of the stop hole decreases the size of the stop hole during the crimping of the proximal end, with the result that the axis of the stop hole may displace toward the lower die. This causes a problem same as that described above. In addition, adjusting the flat face of the thread guide so that the flat face is located at the same level as the edge of the stop hole leads to another problem. That is, a suture thread, if it is not stiff, moves along the inclining face, strikes against the face of the proximal end of the suture needle, and is hindered from being inserted into the stop hole smoothly.

In particular, where no inclining face is formed on the thread guide and each flat face is located so as to correspond to the edge of the stop hole, a suture thread is able to be guided into the stop hole smoothly. However, this may lead to the problem that a level difference between the flat face of the thread guide and the edge of the stop hole reduced in size increases and, consequently, a significant shearing force acts thereon.

Unlike the technique disclosed in the Patent Document 1, in which the upper and lower dies are composed of a movable and fixed die respectively, another proposed crimping device performs crimping by moving two movable dies the same distance relative to the axis of a medical suture needle. This crimping device is free from such a problem as the thread guide's exerting a shearing force on a suture thread. However, this type of crimping device suffers from the problem that maintenance or the adjustment of the thickness of the medical suture needle to be crimped is extremely troublesome.

It is accordingly an object of the present invention to provide a crimping device that is able to insert a suture thread into a stop hole smoothly, and is able to prevent a shearing force from being exerted on the suture thread.

Means for Solving the Problems

In order to overcome the foregoing problem, there is provided a crimping device configured such that a medical suture thread inserted in a stop hole formed in a face of the proximal end of a medical suture needle is bonded to the medical suture needle by crimping the proximal end. The crimping device includes: a crimping die including a fixed die and a movable die that moves away from or toward the fixed die; and a thread guide that approaches an edge of the stop hole formed in the face of the proximal end of the medical suture needle held by the crimping die, thereby guiding the medical suture thread into the stop hole. The thread guide is disposed so that, when the proximal end of the medical suture needle is crimped by the crimping die, the thread guide does not exert an external force on the suture thread exposed on the outside of the stop hole formed in the medical suture needle as a crimping operation with the crimping die progresses; alternatively, the thread guide is moved in a direction in which the thread guide does not exert an external force on the suture thread exposed on the outside of the stop hole in the medical suture.

Effect of the Invention

The crimping device according to the present invention has a guide face that approaches the edge of a stop hole formed in the face of the proximal end of a medical suture needle held by crimping dies. This makes it easy to insert a suture thread into the stop hole by moving the suture thread along this guide face.

In particular, the thread guide is disposed so as to prevent an external force from acting on a suture thread as a crimping operation of the proximal end of a medical suture needle progresses. Alternatively, the thread guide is configured so as to move in the direction in which an external force is prevented from acting on the suture thread. This prevents a suture thread from becoming subject to a shearing force or thus being damaged.

EXPLANATIONS OF LETTERS OR NUMERALS

A crimping DEVICE
B crimping DIE
C THREAD GUIDE
1 FIXED DIE
2 MOVABLE DIE
10 X-Y TABLE
11 FRAME
12 SHAFT
13 LEVER
14 SPRING
15, 16 RESTRICTING MEMBER
18 SETTING MEMBER
18a SPRING
19 DRIVE MEMBER
19a ECCENTRIC COLLAR
19b CONNECTION BAR
21 BLOCK
21a FIRST FLAT FACE
21b SECOND FLAT FACE
21c INTERSECTION
21d CONTACT FACE
22 CUSHION MEMBER
23 PRESSING MEMBER

BEST MODES FOR CARRYING OUT THE INVENTION

Hereinafter most preferred current embodiments of a crimping device of the present invention will be described. The crimping device according to the present invention inserts a suture thread into a stop hole of a medical suture needle (hereinafter referred to as an "eyeless needle"), which has at its one end a needle point that is inserted in the tissue of a living body and at the other end, i.e., the proximal end, the stop hole formed in the face thereof. The crimping device then crimps the area corresponding to the stop hole in the face of the proximal end of the eyeless needle, thereby bonding the suture thread to the eyeless needle.

In particular, the device is arranged such that a thread guide is disposed or moved in order to prevent an external force, especially, a shearing force, from acting on a suture thread exposed on the outside of a stop hole in an eyeless needle as a crimping operation for the proximal end of the eyeless needle progresses, while this proximal end is held between a pair of crimping dies.

First Embodiment

Figure 1:
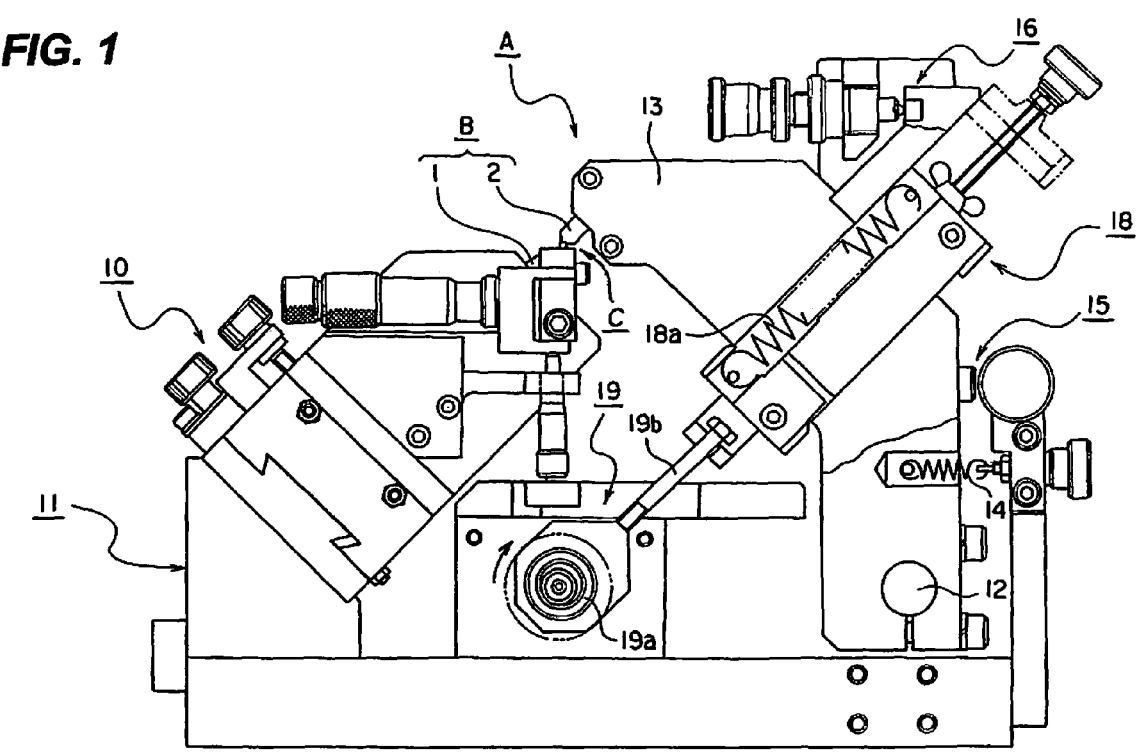
FIG. 1 is a side view of a crimping device.

First, the entire configuration of a crimping device according to the present embodiment will be explained briefly with reference to the accompanying drawings. FIG. 1 is a side view of the crimping device. The configuration of the basic structure of the crimping device A according to the present embodiment is the same as that described in the Patent Document 1 described above. Therefore, a mechanism for crimping the eyeless needle is explained briefly with reference to FIG. 1.

The crimping device A shown in FIG. 1 has a crimping die B that includes a fixed die 1, and a movable die 2 that moves away from or toward the fixed die 1. The fixed die 1 is attached to a frame 11 of the crimping device A via an X-Y table 10 that adjusts the position of the fixed die 1 in relation to the movable die 2. The movable die 2 is attached to a lever 13 fixed to a shaft 12 supported by a bearing (not shown) so as to be rotatable.

As shown in FIG. 13, the lever 13 has an approximately L-shaped form. One end of the lever 13 is fixed to the shaft 12, and the movable die 2 is attached to the other end. Accordingly, such force as with which the lever 13 moves toward the fixed die 1 acts on the lever 13 constantly. A spring 14 is adjusted relative to this force such that force is applied to the movable die 2 in the direction in which the movable die 2 moves away from the fixed die 1. Thereby force applied to the movable die 2 relative to the fixed die 1 is adjusted, so that the eyeless needle can be held by means of the crimping die B.

The range of rotation of the lever 13 around the shaft 12 is restricted by restricting members 15 and 16. A crimping allowance in relation to the eyeless needle is set in advance according to the thickness of the eyeless needle. Each time the thickness of the eyeless needle to be crimped changes, the restricting members 15 and 16 are adjusted to provide the optimum crimping allowance.

The lever 13 is provided with a setting member 18, which sets the crimping force required to crimp the eyeless needle. A drive member 19 is connected to the lever 13 via the setting member 18. When the drive member 19 is driven, a pre-set force acts on the movable die 2 attached to the lever 13. Thereby the movable die 2 is brought into firm contact with the fixed die 1, thus crimping the eyeless needle.

Specifically, the setting member 18 has a spring 18a and the tension of the spring 18a can be adjusted if necessary. In addition, the drive member 19 has: an eccentric collar 19a rotated and driven by a motor, and a connection bar 19b one end of which is connected to the eccentric collar 19a and the other end of which is connected to the setting member 18. As the motor rotates, the driving member 19 is able to pull the connection bar 19b toward the crimping die B.

A thread guide C is disposed in the vicinity of the crimping die B. The thread guide C has the function of guiding the movement of a suture thread when the suture thread is inserted in the eyeless needle held by the fixed die 1 and the movable die 2 composing the crimping die B.

In the crimping device A of the foregoing configuration, the eyeless needle is held by sandwiching the proximal end of the eyeless needle by means of the crimping die B; and in this state, the suture thread is moved along the thread guide C and inserted into a stop hole formed in the face of the proximal end of the eyeless needle. Subsequently, the motor is driven to cause a force to act on the lever 13, via the connection bar 19b and setting member 18, in the direction in which the movable die 2 is brought into firm contact with the fixed die 1. Thereby the proximal end of the eyeless needle is crimped and thus the suture thread can be connected to the eyeless needle.

When the eyeless needle is crimped in a manner as described above, holding force to hold the eyeless needle can be adjusted to a required size by adjusting a spring 14. crimping force to crimp the eyeless needle can be adjusted to a required size by adjusting the spring 18a of the setting member 18. Accordingly, adjusting these as required makes it possible to crimp the eyeless needle with an appropriate crimping force that matches the thickness of the eyeless needle.

Second Embodiment

Figure 2:
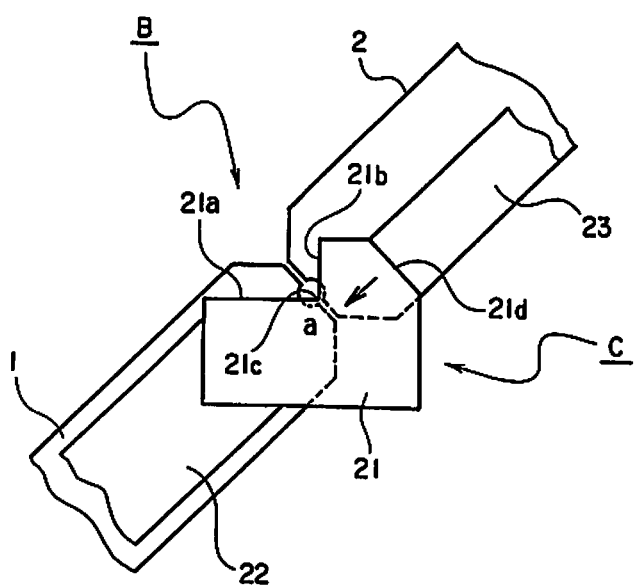
FIG. 2 is a side view explaining the relation between the crimping die and the thread guide.
Figure 3:
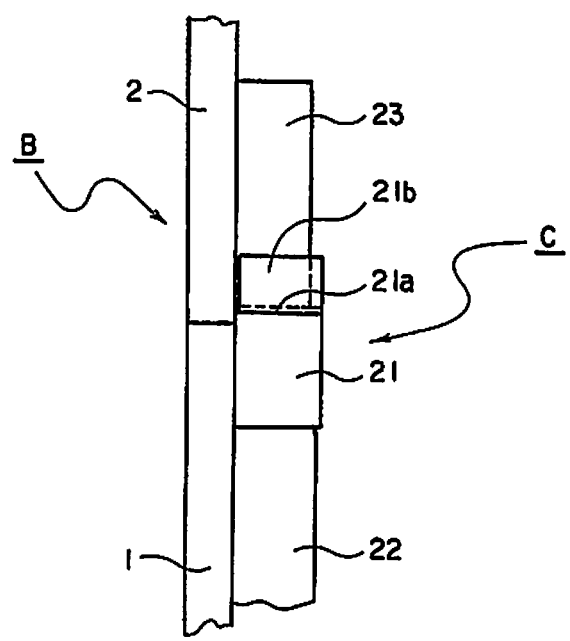
FIG. 3 is a front view explaining the relation between the crimping die and the thread guide.

Next the relation between the crimping die B and the thread guide C will be described. FIG. 2 is a side view explaining the relation between the crimping die and the thread guide. FIG. 3 is a front view explaining the relation between the crimping die and the thread guide.

The thread guide C includes an L-shaped block 21, and has a first flat face 21a serving as a guide face disposed horizontally and a second flat face 21b serving as a guide face disposed vertically. The flat faces 21a and 21b meet substantially at a right angle at the intersection 21c. In order that they intersect precisely at a right angle at the intersection 21c, it is preferable that the following method be adopted: two rectangular parallelepipedic blocks are formed, the flat faces 21a and 21b are formed independently on the corresponding blocks, and these blocks are connected together by, for example, bolts. Depending on the thickness of a suture thread, the intersection 21c does not have to be precisely at a right angle, in which case, the face may be formed by a cutting process using a tool such as an end mill or milling cutter or by a discharging process.

The block 21 is attached to the X-Y table 10 via a cushion member 22. The cushion member 22 is made of a material of sufficient elasticity (e.g., synthetic resin including urethane foam, rubber, etc.). When an external force acts on the block 21, the block 21 deforms according to the external force so as to absorb it.

On a specific higher part of the block 21, a contact face 21d is formed, with which a pressing member 23 comes into contact. In synchronization with the crimping operation of the movable die 2 of the crimping die B, the pressing member 23 moves in the same direction as the movable die 2. Accompanying this movement, the block 21, composing the thread guide C, can be moved in the direction of the arrow a.

It is enough for the pressing member 23 to have a function such as to move the block 21 in the direction of the arrow a in synchronization with the crimping operation of the movable die 2, that is, the crimping operation by the lever 13. The pressing member 23, therefore, does not have to be configured integrally with the movable die 2. In addition, the degree of movement of the pressing member 23 in the direction of the arrow a does not have to be equal to that of movement of the movable die 2 but may be half the degree of movement of the movable die 2.

The degree of movement of the block 21 in the direction of the arrow a due to the crimping operation differs according to the way in which the block 21 is disposed. Specifically, in the case where both the flat faces 21a and 21b are disposed so as to cross the direction of movement of the movable die 2, as shown in FIG. 2, when the flat faces 21a and 21b move by the same degree as does the movable die 2 due to crimping, the first flat face 21a separates from the suture thread whereas the second flat face 21b comes into contact with the suture thread and exerts a shearing force on this thread. To prevent this, in the present embodiment, the block 21 is arranged to move in the direction of the arrow a by only half the degree of movement of the movable die 2.

In addition, in the case where the first flat plate 21a of the block 21 is disposed perpendicular to the direction of the arrow a and the second flat face 21b is disposed parallel to the arrow a, the second flat face 21b does not come into contact with a suture thread when crimping toward the movable die 2 is in progress. Accordingly, it is sufficient that the degree of movement of the block 21 in the direction of the arrow a be half or more of the degree of movement of the movable die 2.

As described above, the degree of movement of the block 21 due to the crimping operation is determined by the angle of each of the flat faces 21a and 21b to the direction of movement of the movable die 2. It is, therefore, preferable that the position of the block 21 composing the thread guide C be determined taking into account of, for example, the ease of handling of the dies of the crimping device.

The disposition and position of the block 21 are not limited only to those shown in FIG. 2, but may be axisymmetrical to the direction of movement of the movable die 2.

Therefore, the following configuration may be adopted: a stand (not shown) is set up in a frame 11, and the pressing member 23 is disposed on the stand movably and connected to the lever 13 with a gear or the like disposed between them; thereby the block 21 is moved in the direction of the arrow a in synchronization with the crimping operation of the lever 13.

The present embodiment adopts the simplest structure in which the pressing member 23 is integrally held by the movable die 2.

In the crimping device A of the foregoing configuration, a suture thread is moved along the flat faces 21a and 21b of the block 21, with the eyeless needle held and maintained between the fixed die 1 and movable die 2; thereby the suture thread can be inserted in the stop hole formed in the eyeless needle. In this state, the lever 13 is then driven to move the movable die 2 closer to the fixed die 1. As the movable die 2 comes closer to the fixed die 1, the proximal end of the eyeless needle is crimped and, in addition, the block 21 is moved in the direction of the arrow a by the pressing member 23.

Simultaneously with the crimping operation for the eyeless needle, the block 21 composing the thread guide C is moved in the direction of arrow a. Thereby, the block 21 is moved in the same direction as the movable die 2. This reduces the size of the stop hole in the face of the proximal end of the eyeless needle. Accordingly, the flat faces 21a and 21b are prevented from bending the suture thread bonded to the stop hole. Thus, a shearing force is prevented from being exerted on the suture thread.

After the crimping operation for the eyeless needle finishes, the drive of lever 13 stops. Then, in order to separate the eyeless needle from the crimping die B, the movable die 2 is moved away from the fixed die 1. As the movable die 2 moves away from the contact face 21d, the pressing member 23 moves away from the contact face 21d of the block 21. Consequently, the block 21 is subject to the elasticity of the cushion member 22, and returns to its original position, that is, its initial position where the block 21 is located in the vicinity of the fixed die 1.

In the present embodiment, the block 21 composing the thread guide C is configured to move in the direction of the arrow a in synchronization with the crimping operation of the movable die 2. However, the present invention is not limited to this configuration but may be configured to rotate the block 21 in synchronization with the crimping operation. In this case, as the pressing member 23 moves in the direction of the arrow a, the first face 21a is simply rotated so as to recede in the same direction as the arrow a.

In the present embodiment, the first and second flat faces 21a and 21b of the block 21 composing the thread guide C are disposed horizontally and vertically respectively. However, the present invention is not limited to these dispositions. The first and second flat faces may be disposed perpendicular and parallel, respectively, to the direction of the movement of the movable die 2. The first and second flat faces may be disposed in any other directions as long as they are disposed so as to prevent their bending a suture thread when pressed and moved by the pressing member 23.

Third Embodiment

Figure 4:
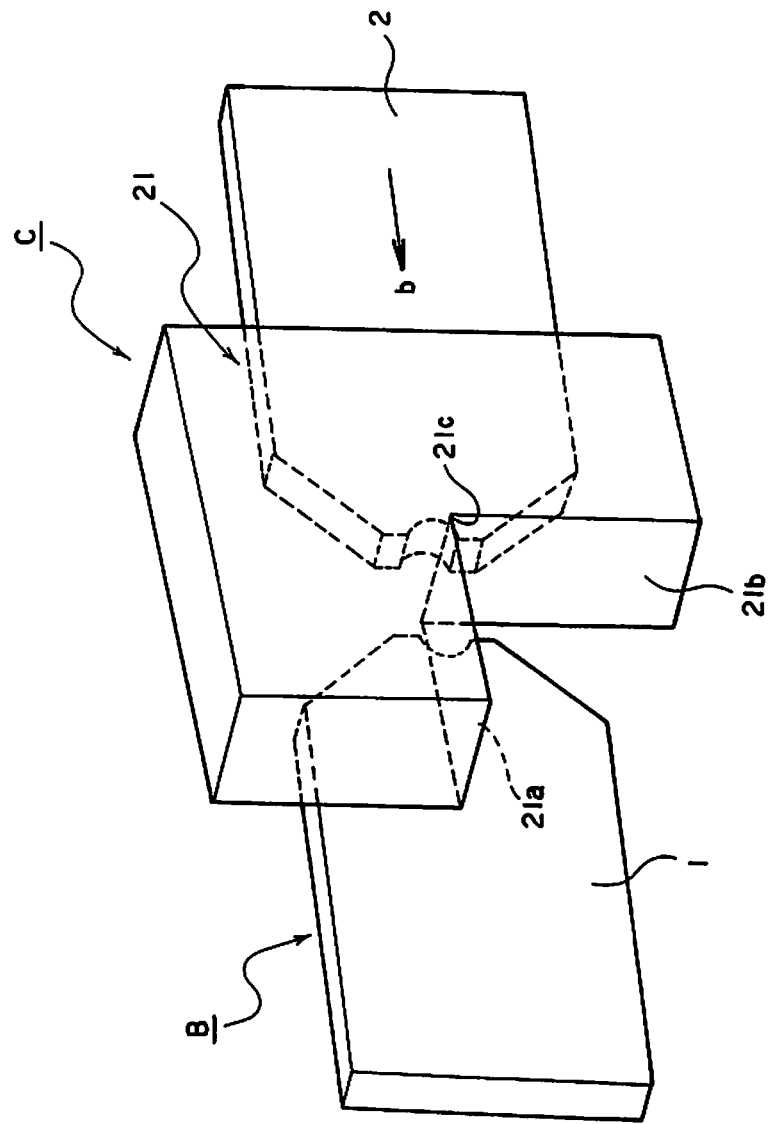
FIG. 4 is a perspective view explaining the relation between the crimping die and the thread guide in another example.
Figure 5A:
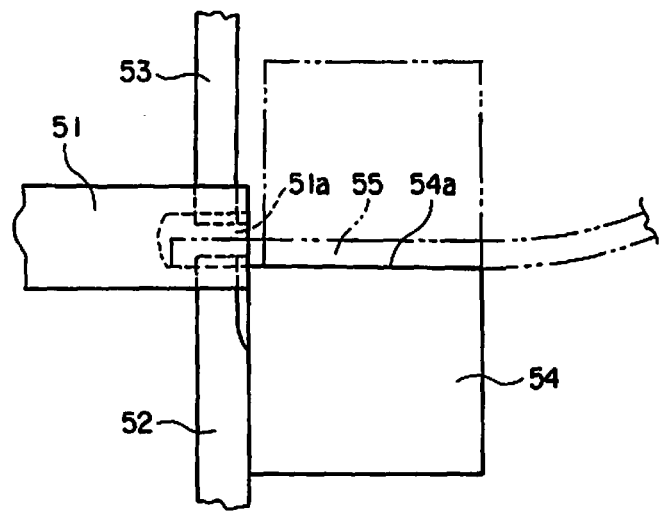
FIGS. 5A and 5B are a view illustrating the problems.
Figure 5B:
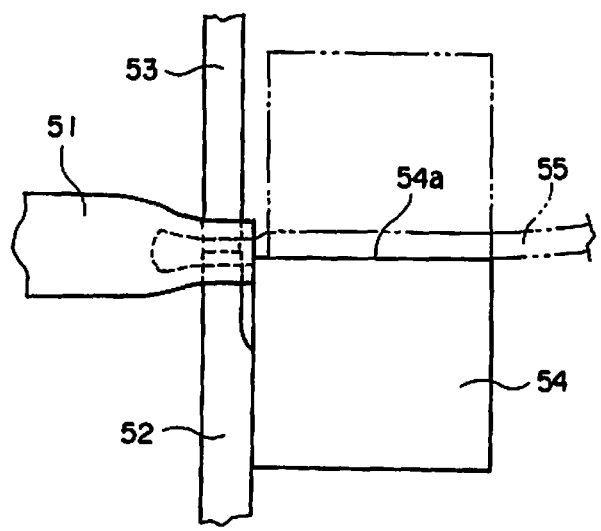

FIG. 4 is a view illustrating the configuration in which the thread guide C is disposed such that, when the eyeless needle is crimped, an external force is not exerted on a suture thread bonded to the eyeless needle.

As shown in FIG. 4, in the block 21 composing the thread guide C, the first flat face 21a is disposed parallel to the direction of arrow b, which is the direction of movement of the movable die 2, and the second flat face 21b is disposed perpendicular to the direction of the arrow b and further upstream of the first flat face 21a in the direction in which the movable die 2 is moved during crimping.

In the present embodiment, while the eyeless needle is held between the fixed die 1 and the movable die 2, a suture thread is moved along each of the flat faces 21a and 21b of the block 21, thereby enabling the suture thread to be inserted through the stop hole formed in the eyeless needle. In this state, the lever 13 is driven to move the movable die 2 closer to the fixed die 1, thereby crimping the proximal end of the eyeless needle as the movable die 2 approaches. In this case, accompanying this crimping operation, the stop hole formed in the proximal end of the eyeless needle is reduced in size in the direction of the fixed die 1 (i.e., in the direction of the arrow b.

Consequently, as the crimping operation for the eyeless needle progresses, the suture thread separates from the second face 21b (i.e., in the direction of the arrow b along the first flat face 21a of the block 21. This prevents the suture thread from being bent or subject to a shearing force.

The position of the block 21 composing the thread guide C is not limited to that shown in FIG. 4. The block 21 may be positioned axisymmetrical to the direction of movement of the movable die 2. In this case also, as the crimping operation for the eyeless needle progresses, the suture thread separates from the second flat face 21b (i.e., in the direction of the arrow b along the second flat face 21b of the block 21. This prevents the suture thread from being bent or subject to a shearing force.

In each of the embodiments described above, as the block 21 composing the thread guide C, any block may be used as long as the flat faces 21a and 21b are formed flat. A block of metal, resin, or the like, or a block whose surface is coated with another material can be used; the material of the block is not limited in particular.

INDUSTRIAL APPLICABILITY

A crimping device according to the present invention prevents, when a suture thread is bonded to an eyeless needle, a shearing force from acting on the suture thread. This makes it possible to stabilize the quality of a medical suture needle to which a suture thread is bonded, thus yielding advantageous effects.

The invention claimed is:

1. A crimping device which bonds a medical suture thread inserted in a stop hole formed in a face of a proximal end of a medical suture needle to the medical suture needle by crimping the proximal end, comprising:
   a crimping die including a fixed die and a movable die that moves away from or toward the fixed die;
   a thread guide that has a surface which is disposed to guide the medical suture thread into the stop hole and the thread guide has a portion of the thread guide that is adjacent to an edge of the stop hole of the medical suture needle, and
   a pressing member contacting the thread guide, the pressing member being structured and arranged to move the thread guide in a same direction as the movable die in synchronization with a crimping operation of the movable die when the movable die approaches the fixed die.

2. A crimping device according to claim 1, wherein the thread guide is formed of first and second flat faces which form a substantially L-shape.

3. A crimping device according to claim 2, wherein the first and second flat faces are disposed at an angle to a direction of movement of the movable die, and an amount of movement of the thread guide due to a crimping operation is half of an amount of movement of the movable die.

4. A crimping device according to claim 2, wherein the first flat face is disposed perpendicular to a direction of movement of the movable die, the second flat face is disposed parallel to the direction of movement of the movable die, and an amount of movement of the thread guide due to a crimping operation is at least half of an amount of movement of the movable die.

5. A crimping device according to claim 2, wherein the first and second flat faces are disposed approximately 45 degrees to a direction of movement of the movable die.

6. A crimping device which bonds a medical suture thread inserted in a stop hole formed in a face of a proximal end of a medical suture needle to the medical suture needle by crimping the proximal end, comprising:
- a crimping die including a fixed die and a movable die that moves away from or toward the fixed die; and
- a thread guide that has a surface which is disposed to guide the medical suture thread into the stop hole and the thread guide has a portion of the thread guide that is adjacent to an edge of the stop hole of the medical suture needle, wherein the thread guide is structured and arranged to rotate in synchronization with a crimping operation.

7. A crimping device which attaches a medical suture thread inserted in a stop hole formed in a face of a proximal end of a medical suture needle to the medical suture needle by crimping the proximal end, comprising:
- a crimping die including a fixed die and a movable die that moves away from or toward the fixed die; and
- a thread guide that has a surface which is disposed to guide the medical suture thread into the stop hole and the thread guide has a portion of the thread guide that is adjacent to an edge of the stop hole of the medical suture needle,
- wherein the thread guide is formed of first and second flat faces which form a substantially L shape, the first flat face is disposed parallel to a direction of movement of the movable die, and the second flat face is disposed perpendicular to the direction of movement of the movable die, the first flat face having a first end closer to the fixed die and a second end closer to the movable die, the second flat face having a first end adjacent to the second end of the first flat face and a second end farther from the second end of the first flat face, and the first end of the second flat face is closer to the movable die than the first end of the first flat face at a beginning of a crimping operation.

8. A crimping device which attaches a medical suture thread inserted in a stop hole formed in a face of a proximal end of a medical suture needle to the medical suture needle by crimping the proximal end, comprising:
- a crimping die including a fixed die and a movable die that moves away from or toward the fixed die; and
- a thread guide that approaches an edge of the stop hole of the medical suture needle held by the crimping die and has a surface which guides the medical suture thread into the stop hole, wherein the thread guide is formed of first and second flat faces, which serve as guide faces, so as to have a substantially L shape, the first and second flat faces are axisymmetrical to a direction of movement of the movable die, and an intersection of the first and second flat faces is located above the first and second flat faces in a direction of a crimping movement of the movable die.

9. A crimping device for attaching a medical suture thread in a stop hole formed in a medical suture needle, comprising:
- a crimping die including a fixed die and a movable die that moves toward and away from the fixed die;
- a thread guide having a surface disposed to allow guidance of the medical suture thread into the stop hole, wherein the thread guide is formed of first and second flat surfaces that are disposed at an angle of less than 180 degrees; and
- a pressing member contacting the thread guide, the pressing member being structured and arranged to move the thread guide in a same direction as the movable die in synchronization with a crimping operation of the movable die when the movable die approaches the fixed die.

10. A crimping device according to claim 9, wherein the first and second flat surfaces are disposed to be maintained symmetrical to a direction of movement of the movable die.

11. A crimping device according to claim 9, wherein the first and second flat surfaces are rotated relative to a direction of movement of the movable die.

12. A crimping device according to claim 9, wherein the first and second flat surfaces which form a substantially L-shape, and the thread guide is able to move in a same direction as the movable die in synchronization with a crimping operation of the movable die.

13. A crimping device according to claim 9, wherein the first and second flat surfaces are disposed at an angle to a direction of movement of the movable die, and an amount of movement of the thread guide due to a crimping operation is half of an amount of movement of the movable die.

14. A crimping device according to claim 9, wherein the first flat surface is disposed perpendicular to a direction of movement of the movable die, the second flat surface is disposed parallel to the direction of movement of the movable die, and an amount of movement of the thread guide due to a crimping operation is at least half of an amount of movement of the movable die.

15. A crimping device according to claim 9, wherein the first and second flat surfaces are disposed approximately 45 degrees to a direction of movement of the movable die.

16. A crimping device according to claim 9, wherein the thread guide is able to rotate in synchronization with a crimping operation.

17. A crimping device according to claim 9, further comprising a cushion member for cushioning the thread guide during a crimping operation.

* * * * *